(12) United States Patent
Bhardwaj

(10) Patent No.: US 12,268,893 B2
(45) Date of Patent: Apr. 8, 2025

(54) PHOTOTHERAPY FACE MASK

(71) Applicant: Light Tree Ventures Holding B.V., The Hague (NL)

(72) Inventor: Yogesh Bhardwaj, New Delhi (IN)

( * ) Notice: Subject to any disclaimer, the term of this patent is extended or adjusted under 35 U.S.C. 154(b) by 813 days.

(21) Appl. No.: 17/237,070

(22) Filed: Apr. 22, 2021

(65) Prior Publication Data

US 2022/0339462 A1 Oct. 27, 2022

(51) Int. Cl.
*A61N 5/06* (2006.01)
*A61M 37/00* (2006.01)

(52) U.S. Cl.
CPC .............. *A61N 5/062* (2013.01); *A61M 37/00* (2013.01); *A61M 2210/0606* (2013.01); *A61N 2005/0626* (2013.01); *A61N 2005/0647* (2013.01); *A61N 2005/0652* (2013.01)

(58) Field of Classification Search
CPC ............ A61N 5/062; A61N 2005/0647; A61N 2005/0626; A61N 2005/0652; A61M 37/00; A61M 2037/0007; A61M 2210/0606; A61M 35/10; A61M 35/003
See application file for complete search history.

(56) References Cited

U.S. PATENT DOCUMENTS

| | | | | |
|---|---|---|---|---|
| 5,169,251 A | * | 12/1992 | Davis ................ | A61M 35/003 401/266 |
| 5,913,883 A | * | 6/1999 | Alexander .......... | A61N 5/0616 D24/231 |
| 10,105,548 B2 | | 10/2018 | Mofar | |
| 2004/0147984 A1 | * | 7/2004 | Altshuler ............ | A46B 13/023 607/88 |
| 2005/0070977 A1 | | 3/2005 | Molina | |

(Continued)

FOREIGN PATENT DOCUMENTS

| | | | |
|---|---|---|---|
| CN | 106390301 A | * | 2/2017 |
| KR | 100963687 B1 | * | 6/2010 |
| KR | 101823263 B1 | * | 9/2016 |

OTHER PUBLICATIONS

Prior art pertinent to applicant's disclosure KR 100963687 B1 (Year: 2010).*

(Continued)

*Primary Examiner* — Nilay J Shah
(74) *Attorney, Agent, or Firm* — Emanus LLC; Willie Jacques

(57) ABSTRACT

A phototherapy face mask is provided for emitting therapeutic radiation towards the facial region of a user and aims to restore the youthful appearance of the user who is wearing the mask. The phototherapy mask comprises an outer surface and an inner surface, wherein the inner surface is aligned with the facial skin of the user. A flexible PCB layer is provided between the inner surface and the outer surface, on which a plurality of coherent light sources such as LEDs are mounted. The light sources are configured to emit radiation preferably in the visible and infrared range of the electromagnetic spectrum. The mask further includes a medicament chamber which is operably coupled to a piezoelectric pump that dispenses the medicament at regular intervals. The medicament is uniformly distributed all over the facial region of the user through a plurality of pores of the mask.

11 Claims, 5 Drawing Sheets

(56) References Cited

U.S. PATENT DOCUMENTS

| | | | |
|---|---|---|---|
| 2008/0032119 A1* | 2/2008 | Feldhahn | A61M 16/0825 428/332 |
| 2008/0255498 A1* | 10/2008 | Houle | A61C 17/0208 604/20 |
| 2011/0144410 A1* | 6/2011 | Kennedy | A61N 5/0616 600/2 |
| 2018/0352937 A1* | 12/2018 | Vandier | A61B 5/6803 |

OTHER PUBLICATIONS

Prior art pertinent to applicant's disclosure KR 101823263 B1 (Year: 2018).*

* cited by examiner

PHOTOTHERAPY FACE MASK

TECHNICAL FIELD

The subject matter of the present invention relates generally to wearable therapeutic devices. More specifically, the subject matter of the present invention relates to a face mask providing light therapy for the treatment of at least one disorder and/or disease related to human facial skin and achieving facial skin rejuvenation benefits including cosmetic and anti-aging benefits.

BACKGROUND ART

The human skin is a large and highly complex organ, consisting of different layers and cell types. It serves as a barrier between the external environment and the inside of the body. The skin fulfills a large range of functions, including prevention of percutaneous water loss, temperature maintenance, sensory perception, and immune surveillance. However, the aging of organs begins from the time when one is born, and there is no exception for the skin. As one ages, their skin more specifically facial skin begins to deteriorate and becomes less elastic. One facial skin gets lose and stretches out in different places. A loss of both function and structural stability in skin proceeds unavoidably as individuals age, which is the result of both intrinsic and extrinsic processes, which contribute simultaneously to a progressive loss of skin integrity. Skin aging leaves several impacts on facial skin and will affect one's outer appearance in the form of skin pigmentation, wrinkles, dark lines, etc.

Depending on the anatomical site the human skin may be affected by both: intrinsic and extrinsic aging. This is especially true for the face, which is exposed to numerous environmental factors during the whole life course. Additionally, repeated facial expressions aggravate the formation of wrinkles. The appearance of the facial skin is most important for the perceived age. In western societies, females seem to be very concerned about their facial appearance and visible aging phenomena indicated by increasing expenditures for cosmetic products and aesthetic procedures. To prevent skin aging, loosening of facial skin various facial rejuvenation techniques have been introduced in the prior art.

The term "Facial skin rejuvenation" refers to a combination of cosmetic treatments, which aims to restore the youthful appearance of a human face. Facial rejuvenation can be achieved through either surgical and/or non-surgical options. These procedures may vary in invasiveness and depth of treatment. However, there are different procedures out there that can be used to rejuvenate one's facial appearance without having to undergo surgery. Facial rejuvenation using light therapy or phototherapy mask is a well-known technique in prior art.

Currently, the available light therapy mask includes the plurality of light sources which can be a laser and/or an LED light source, emits therapeutic radiation, more preferably in the visible and infrared range of electromagnetic spectrum increases circulation and stimulate collagen, making it useful for those who are looking to reduce the appearance of lines, wrinkles and wants to regain their skin integrity. However, these devices are limited to only therapeutic light sources, they don't employ any pharmaceutical composition, medicament, or any other photoactivation agent which will enhance the efficacy of these products and maintains the elasticity of one's face. Moreover, in present devices due to lack of photoactivation agent, the radiation emitted by the light sources is not completely absorbed by the skin cells and some part of the radiation is wasted in atmosphere surroundings. Further to this, in a few other prior art devices, the dispensed medicament is not completely available for the exposed skin surface thereby having an increased bio non-availability of the medicament and reduced efficacy of the treatment. This increased bio non-availability of the medicament and reduced efficacy impact the quality of the therapeutic effect of the light therapy.

The U.S. patent Ser. No. 10/105,548B2 discloses a facial treatment device and a system including the treatment device combining light and electromagnetic therapy for facial treatments. The facial treatment device includes a mask base; a plurality of light-emitting diodes (LEDs) disposed across an inner side of the facial treatment device; and one or more electromagnetic field producing units, each configured for producing an electromagnetic field located over the periphery of the mask base. However, the device mentioned in the patent document does not have any medicament chamber and any photo-activating agent which improves the anti-aging benefits of the device.

Further, the US patent US20050070977A1 discloses a therapeutic mask includes light-emitting diodes and electromagnets embedded in the mask. Pulsed light and pulsed magnetic energy are emitted to a user's facial region. Facial therapy is performed with the mask simultaneously or separately using magnetic therapy and light therapy. The electro-pulsed magnets are embedded in the mask at appropriate locations based on acupressure and acupuncture therapy. Diodes in the mask are located about the center of the electromagnetic to maximize therapeutic results. However, the device mentioned in the patent document does not have any medicament chamber that contains pharmaceutical compositions including oil which softens the skin cells and uniformly distributes the radiations emitted by the face mask.

However, even though there are several phototherapy masks in the art, but none of them incorporates a treatment protocol or method of using pharmaceutical composition along with the light therapy benefits. Furthermore, these devices are lacking uniform distribution of therapeutic radiation all over the facial skin. Moreover, most of the devices available in the art are bulky and are not comfortable, and also require more time to achieve their goal.

Therefore, there is a need for a novel phototherapy face mask that overcomes the disadvantages and limitations associated with the prior art and provides a more satisfactory solution.

OBJECTS OF THE INVENTION

Some of the objects of the present invention are listed below:

It is an object of the present invention to provide a phototherapy mask that rejuvenates the facial skin of a user using light energy and regains the elasticity of the facial skin;

It is another object of the present invention to provide a phototherapy mask comprises a plurality of non-coherent light sources that emit therapeutic radiation more preferably visible and infrared range of the electromagnetic spectrum;

It is another object of the present invention to provide a phototherapy mask includes a medicament chamber to store the pharmaceutical composition which enhances the therapeutic effect produced by the mask;

It is another object of the present invention to provide a phototherapy mask includes a piezoelectric pump that uniformly distributes the medicament all over the facial skin of a user;

It is another object of the present invention to provide a phototherapy mask that supports wireless connectivity and is configured to control by an external communication device;

It is a further object of the present invention to provide a phototherapy mask that completely covers the facial region of a user and have a plurality of openings of nose, eyes, and mouth;

It is yet another object of the present invention to provide a phototherapy mask which is lightweight and is configured to easily wearable by the users having different head size; and It is furthermore the object of the present invention to provide a phototherapy mask that is portable and easy to use.

Other objects, features, advantages, and goals of the present invention will be better understood from the following detailed description taken in conjunction with the accompanying drawings.

SUMMARY OF THE PRESENT INVENTION

The present invention provides an effective and reliable approach for the treatment of facial skin-related disorders and diseases using light energy in the form of a wearable light therapy face mask device.

According to an aspect of the present invention, there is provided a face mask for providing phototherapy to a facial skin of a user, said face mask comprising an inner layer and an outer layer, wherein the inner layer is towards the facial skin of the user and includes a plurality of pores, a flexible printed circuit board (PCB) provided between the inner layer and the outer layer of the face mask, wherein the circuit board includes a plurality of light sources that emits therapeutic radiation towards the facial skin of the user, a medicament chamber enclosing at least one medicament that is uniformly dispensed on the facial skin of the user through the plurality of pores, a plurality of fluid channels positioned inside the inner layer, wherein the fluid channels guide the flow the medicament from the medicament chamber to the pores of the inner layer using a piezoelectric pump and a control unit for controlling the flow of medicament and at least one characteristic of radiation emitted by the said light source, wherein the face mask includes a plurality of openings for nose, eye and mouth region of the user.

In one embodiment of the present invention, the inner surface layer of the face is made of synthetic polymeric material.

In one embodiment of the present invention, the synthetic polymeric material of the inner layer is preferably selected from the group consisting of a polysiloxane material and a polyacrylonitrile material.

In one embodiment of the present invention, the said plurality of light sources is preferably a Light emitting diode (LED).

In one embodiment of the present invention, the plurality of light sources preferably emits radiation in the visible range and infrared range of the electromagnetic spectrum.

In one embodiment of the present invention, the said characteristic of emitted radiation is selected from a group consisting of intensity, frequency, amplitude, and wavelength.

In one embodiment of the present invention, the face mask supports wireless connectivity and is configured to be controlled by an external communication device including the cell phone, the laptop computer, the notebook computer, the tablet computer, and the pocket computer.

In one embodiment of the present invention, the face mask includes an adjustable strap allowing the user to wear the face mask comfortably.

According to an aspect of the present invention, there is provided a method for producing a therapeutic response to an exposed area of the facial skin of a user, said method comprising the following steps:

a) Firstly, wearing a face mask by a user and fixates the face mask using an adjustable strap provided with the said mask;

b) Secondly, selecting a treatment protocol and initializing a therapeutic session of the said face mask;

c) Thirdly, emitting therapeutic radiation by a plurality of light sources in response to the treatment protocol selected by the said user;

d) Fourthly, dispensing a medicament through a medicament chamber using a piezoelectric pump provided within the said face mask;

e) Fifthly, uniformly distributing the said medicament over the facial skin of the user through a plurality of fluid channels provided in the said face mask; and f) Sixthly, receiving a combined therapeutic effect from the said plurality of light sources and the dispensed medicament over the facial skin.

In the context of the specification, the term "medicament" refers to a substance used for medical treatment, wherein medicament includes a drug or pharmaceutical composition which is used to diagnose, cure, treat, or prevent disease.

In the context of the specification, the term "communication network" is considered to be inclusive of Local Area Networks (LANs) be implemented through several short-range wired or wireless communication protocols such as Ethernet, ZigBee, Bluetooth, Wireless Fidelity (Wi-Fi), and Near Field Communication (NFC), etc. and Wide Area Networks (WANs) implemented through protocols standardized by the $3^{rd}$ Generation Partnership Project, such as HSPA, HSDPA, LTE, and the like or through protocols standardized by IEEE such as 802.11 Wi-Fi and 802.3 Ethernet or the like.

In the context of the specification, the term "memory unit" is considered to be inclusive of volatile memory units such as Static Random Access Memory (SRAM) and Dynamic Random Access Memory (DRAM) of types such as Asynchronous DRAM, Synchronous DRAM, Double Data Rate SDRAM, Rambus DRAM, and Cache DRAM, etc.

In the context of the specification, the term "processor" is considered to be inclusive of a general-purpose processor, a Field Programmable Gate Array (FPGA), an ARM-based processor, or an Application Specific Integrated Circuit (ASIC), etc.

The following detailed description is illustrative and is not intended to be in any way limiting. In addition to the illustrative aspects, embodiments, and features described above, further aspects, embodiments, and features will be apparent by reference to the following detailed description in conjunction with the accompanying drawings.

BRIEF DESCRIPTION OF THE ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

Figure 1:
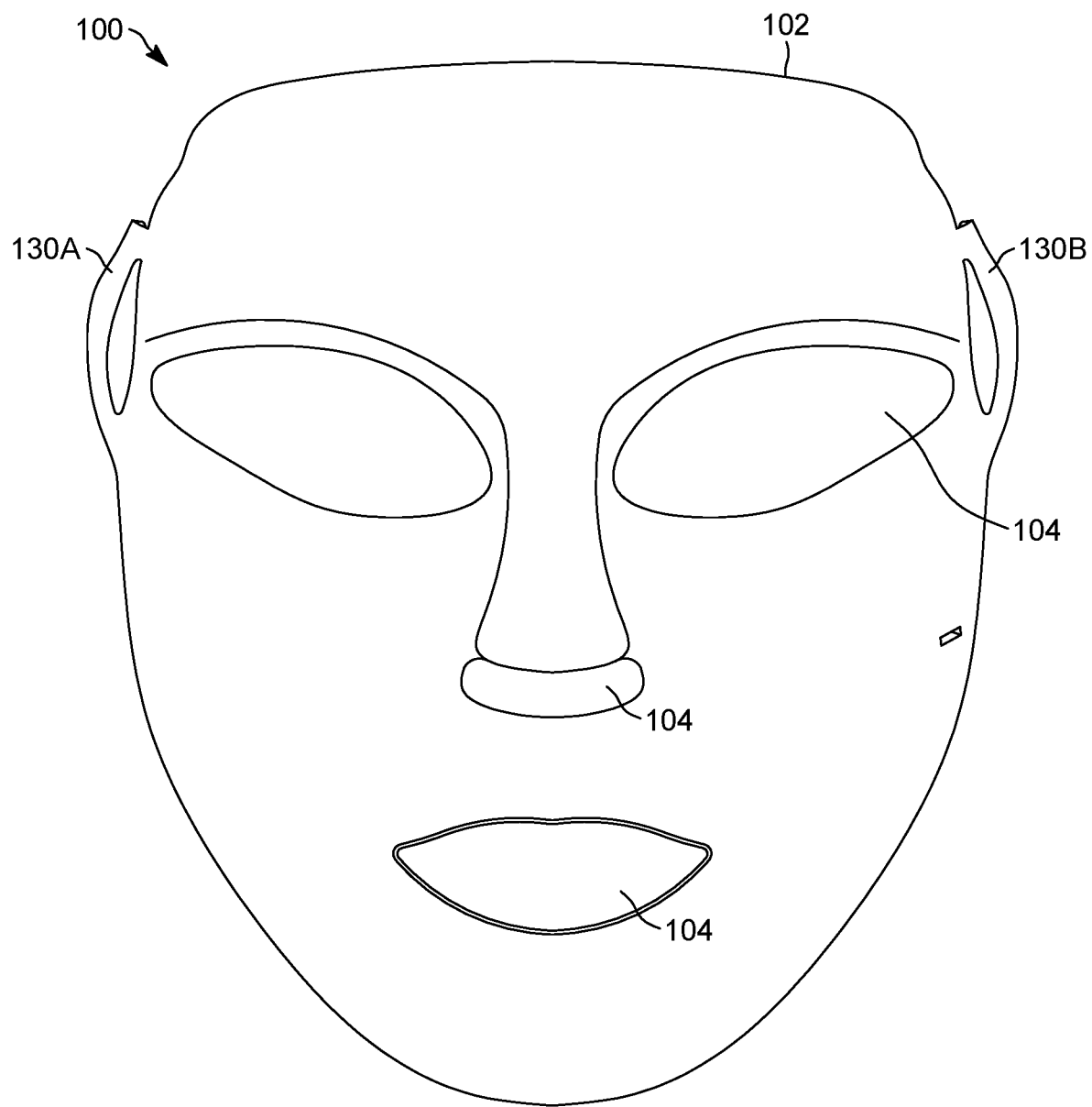
FIG. 1 illustrates a front view of a phototherapy mask in accordance with one embodiment of the present invention.

While the present invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims and equivalents thereof.

DETAILED DESCRIPTION

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

It is envisaged that a phototherapy face mask be provided that emits therapeutic radiation towards the facial region of a user and restores the youthful appearance of the user who is wearing the mask. The phototherapy mask is configured to completely cover the facial region and having a plurality of openings for the nose, eye, and mouth region. The radiation produced by the phototherapy mask rejuvenates the skin cells of the user and thereby reducing the skin aging effects in individuals. The phototherapy mask of the present invention comprises an outer layer and an inner layer, wherein the inner layer is aligned with the facial skin of the user. The inner layer of the phototherapy mask can be made of a synthetic polymeric material that is transparent in nature allowing the light from the light sources to pass therethrough. A flexible PCB board or layer is provided between the outer and inner layer of the phototherapy mask includes a plurality of light sources such as LEDs emitting radiation preferably in the visible and infrared range of the electromagnetic spectrum. However, the phototherapy mask is not limited to only a particular color, it can also emit different color radiation simultaneously or sequentially. For example, the light sources may emit blue light which helps to reduce acne spots, oiliness, scars and may have an anti-inflammatory effect, red light which helps to improve blood circulation, stimulate collagen and reduce the fine lines. Each color and wavelength tackle a different skin problem in order to restore and improve the condition of the skin It is further envisaged that a medicament chamber be provided in the inner layer containing a medicament which can be a photo-activating agent or can be skin-nourishing oil that nourishes or regains the elasticity of the facial skin of a user. The medicament is uniformly distributed all over the facial region of the user using a piezo-electric pump. The piezoelectric is a lightweight diaphragm operably coupled to the medicament chamber and pumps the medicament in the preferred amount from the chamber and dispensed it over the facial skin through the plurality of pores provided on the inner layer of the mask. The inner layer of the phototherapy mask further includes a plurality of fluid channels positioned inside the inner layer, wherein the fluid channels guide the flow of the medicament from the medicament chamber to the pores of the inner layer.

Referring now to FIG. 1, of the present invention illustrating the front view of a phototherapy mask 100. There is shown a phototherapy mask 100 having an outer layer 102 with a plurality of openings 104 provided for eyes, mouth, and nose region of a user 124 (illustrated in FIG. 6). The plurality of openings 104 allows the user 124 to see and breathe comfortably during the therapy session. The phototherapy mask 100 is made of acrylic, plastic, polycarbonate, or other substantially similar material that offers good mechanical and electrical properties throughout the operation of the mask. Polycarbonate material provides up to 89% light transmission while plastic provides 80%. Polycarbonate also provides excellent impact and weather resistance, compared to the resistance provided by the average plastics. It is self-extinguishing and non-inflammable whereas plastic is flammable which leads to damages. In certain embodiments, the phototherapy mask 100 can be made of a polymer preferably acrylamide (or acrylic amide) which is a white-colored odorless solid organic compound increasing the durability of the mask and not subject to the wear and tear of constant bending.

The phototherapy mask 100 is configured in such a way as to completely cover the facial region of the user 124 and conforms to the contour of the user's face with a minimal gap to breathe and sweat within the mask. Furthermore, there is shown a pair of ear loops 130A and 130B provided at the side portions of the phototherapy mask 100. The side portions of the phototherapy mask 100 are flexible enough to accommodate the user's face having different shapes and sizes. An adjustable fastening strap 126 (shown in FIG. 6) is detachably attached to the phototherapy mask 100 through the pair of ear loops 130A and 130B. This arrangement allows the proper fixation of the phototherapy mask 100 to the facial skin of the user 124 in such a way that therapeutic radiation of the phototherapy mask 100 is not wasted in the surroundings and an enhanced facial rejuvenation is achieved. The adjustable strap 126 can be made of an elastic material and can be adjusted as per the size and shape of the user's face.

Figure 2:
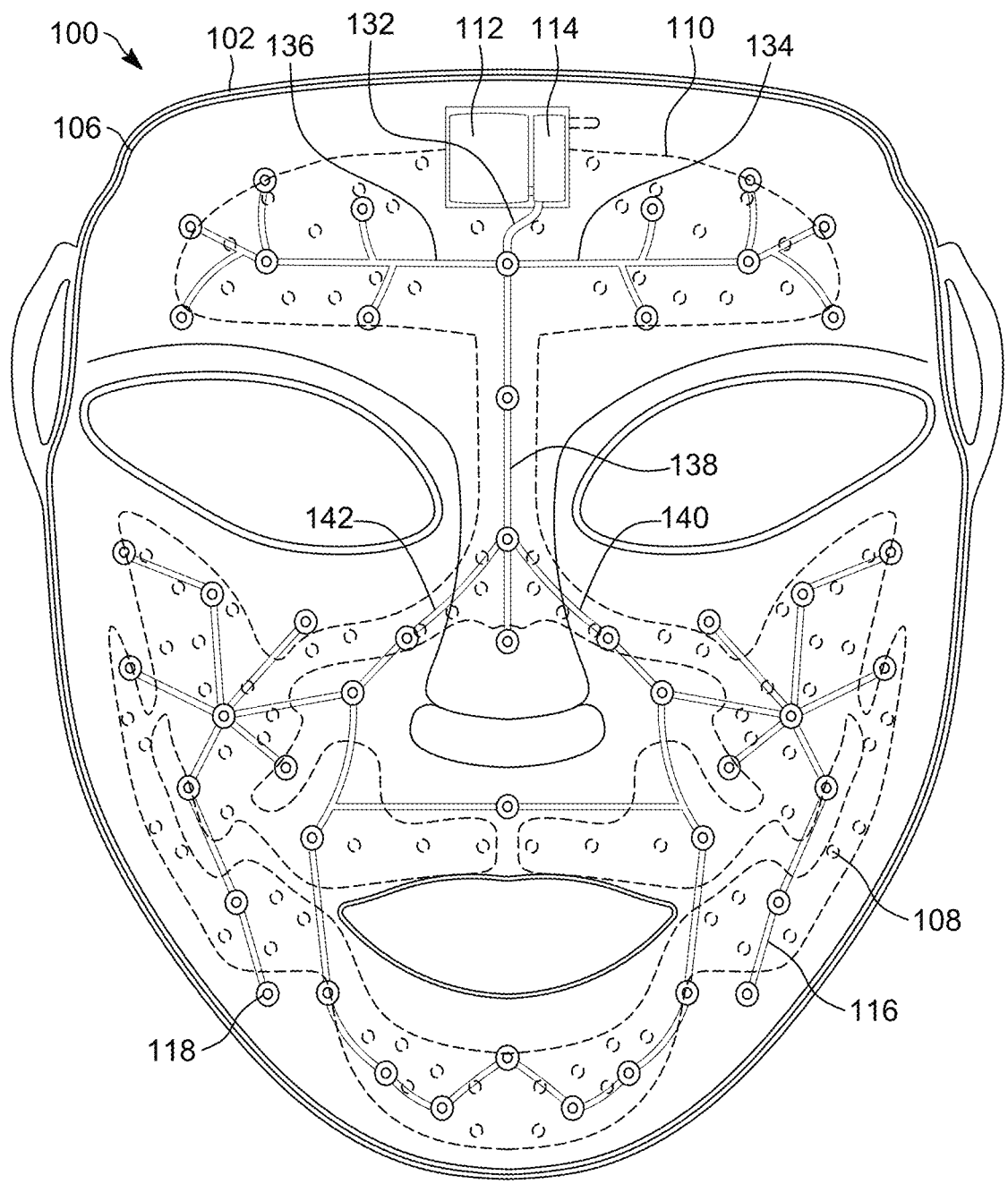
FIG. 2 illustrates a rear view of a phototherapy mask in accordance with one embodiment of the present invention.

Referring now to FIG. 2, illustrating a rear view of the phototherapy mask 100 in accordance with an embodiment of the present invention. There is shown an inner layer 106 which is going to align with the facial skin of the user 124 (shown in FIG. 6) when the phototherapy mask 100 is worn. The inner layer 106 is preferably made up of a synthetic polymeric material that is transparent in nature allowing the light from the light sources to pass therethrough. The synthetic material is less toxic and offers high thermal resistance under certain conditions. The synthetic polymeric material of the inner layer 106 can be selected from a group consisting of a polysiloxane material and a polyacrylonitrile material.

Further, there is shown a plurality of light sources 108 positioned below the inner layer 106 of the phototherapy mask 100 emits therapeutic radiation towards the facial region of the user 124 when activated. The plurality of light sources 108 is generally non-coherent light sources. Preferably, these non-coherent light sources are light emitting diodes [LEDs] which are mounted to the PCB layer 110 (shown in FIG. 3) using surface mounting technology [SMT]. In certain embodiments, the plurality of light source 108 may include other light sources too, for example, laser light source, optical fibers emitting light, organic light emitting diodes [OLEDs]. The plurality of light sources 108 is configured to emit therapeutic radiation preferably in the visible and infrared range of electromagnetic spectrum which will depend upon the treatment mode selected by the user 124. For example, if the visible mode of the phototherapy mask 100 is selected by the user 124, the plurality of light source 108 will emit radiation between the wavelength range of 300 to 700 nm. If a non-visible treatment mode is selected by the user 124, the plurality of light source 108 will emit radiation having a wavelength of more than 650 nm. In certain embodiments, the phototherapy mask 100 will also include a separate treatment mode which includes the combination of visible and non-visible therapeutic radiation. However, the invention is not limited to a particular therapeutic range but may also include the Ultra-violet range (UVA, UVB, and UVC) too which is not harmful to human skin.

A medicament chamber 112 is also illustrated in FIG. 2, contains a medicament that can be a photo-activating agent or can be skin-nourishing oil that nourishes or regains the elasticity of the facial skin of the user 124. The medicament chamber 112 is adapted to deliver a medicament including but not limited to sprays, emollients, gels, pastes, ointments, and medicines in liquid form. The medicament chamber 112 is provided at the top region of the phototherapy mask 100 and is operably coupled to a piezoelectric pump 114. The piezoelectric pump 114 is a thin, compact, and lightweight diaphragm micro-pump which is been specifically designed to pump out the small amount of medicament from the medicament chamber 112 at regular interval. However, the phototherapy mask 100 of the present invention is not limited to piezoelectric pump 114 but may also include other pumps, for example, diaphragm micropumps, peristaltic micropumps, valveless micropumps. In exemplary embodiments, the medicament chamber 112 can also be provided at other regions (including top, bottom, and side portions) of the phototherapy mask 100 which enables the uniform distribution of the medicament over the facial skin of the user 124.

Furthermore, there is provided a plurality of flow channels 116 illustrated in FIG. 2 constructed in the inner layer 106 of the phototherapy mask 100 whose function is to guide the flow of medicament from the medicament chamber 112 to the plurality of pores 118 of the mask 100. The plurality of pores 118, when the medicament is pumped out by the piezoelectric pump 114 dispenses the medicament uniformly all over the facial skin of the user 124. The plurality of pores 118 is configured in such a way on the inner layer 106 of the phototherapy mask 100 that no region of facial skin is left out when the medicament is dispensed. The plurality of flow/fluid channels 116 comprises a main channel 132 originating from the outlet of the medicament chamber 112. The main channel 132 bifurcates into a first channel 134 that covers left forehead area, a second channel 136 that covers right forehead area and a third channel 138 that flows towards nose area. The third channel 138 further bifurcates into a fourth channel 140 that covers left cheek area and a first channel 142 that covers right cheek area. The first channel 134, the second channel 136, the third channel 138, the fourth channel 140 and the fifth channel 142 further bifurcates into sub-channel to cover the facial skin of the user.

Figure 3:
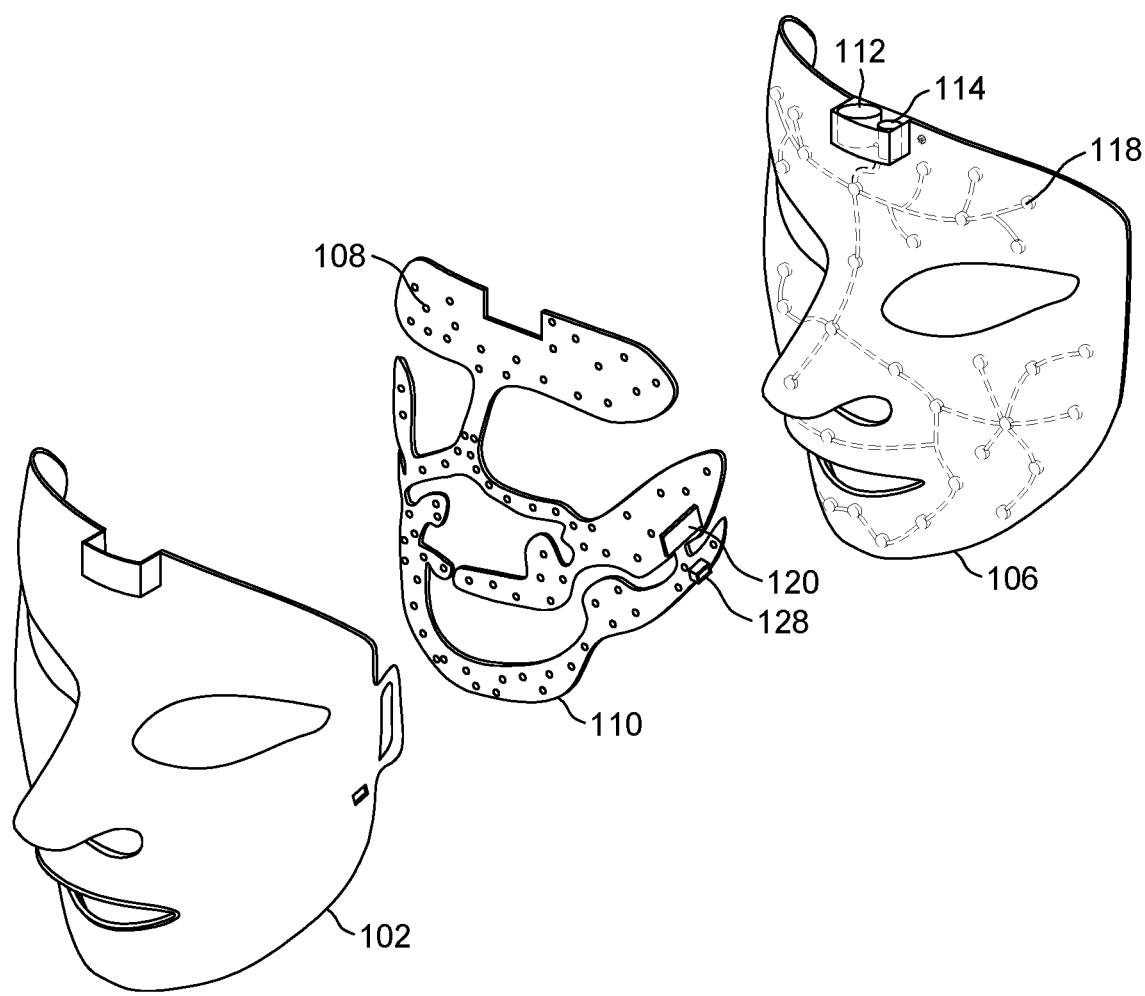
FIG. 3 illustrates an exploded view of a phototherapy mask in accordance with one embodiment of the present invention.

Referring now to FIG. 3 of the present invention, illustrating the exploded view of the phototherapy mask 100. According to the preferred embodiment, the phototherapy mask 100 comprises a three-layer structure, out of which one layer is outer layer 102 facing the exterior surroundings, the layer opposing the outer layer 102 is inner layer 106 contacting the facial skin of the user 124 and the third layer is a flexible printed circuit board (PCB) layer 110 provided between the outer layer 102 and the inner layer 106. The PCB layer 110 further includes a plurality of microelectronic components such as a processor, a storage medium for storing the computing instructions, a plurality of electrical resistors for controlling the flow of current within the phototherapy mask 100, and the plurality of light sources 108 for emitting therapeutic radiation. The plurality of light sources 108 such as light emitting diodes [LEDs] are mounted to the PCB layer 110 through surface mounting technology [SMT]. SMT technology enables smaller PCB designs by allowing more components to be placed closer together on the board. This leads to designs that are more lightweight and compact. Also, the process for production setup is faster when it comes to SMT when compared to through-hole technology. Although not illustrated, the processor comprises a one or more integrated circuit that executes the computing program stored in the storage medium. The storage medium includes a memory unit which can be a read-only memory (ROB/I) storing the computer-related instruction of programming code that facilitates the seamless working of the phototherapy mask 100.

The PCB layer 110 includes a controlling unit 120 which is configured to control the operation of the phototherapy mask 100. More particularly, the controlling unit 120 is responsible for the controlling of one or more characteristics of emitted radiation from the plurality of light sources 108, wherein the characteristics of the emitted radiation are selected from the group consisting of intensity, frequency, amplitude, and wavelength. Furthermore, the controlling unit 120 is also configured to control the flow of medicament from the medicament chamber 112 to the plurality of pores 118 of the inner surface layer 106. The PCB layer 110 further includes a power source 128 for providing electric power to the phototherapy mask 100 for actuating the plurality of light source 108 and piezoelectric pump 114. In certain embodiments, the power source 128 may include a rechargeable or replaceable batteries which can be charged via a charging port.

Figure 4:
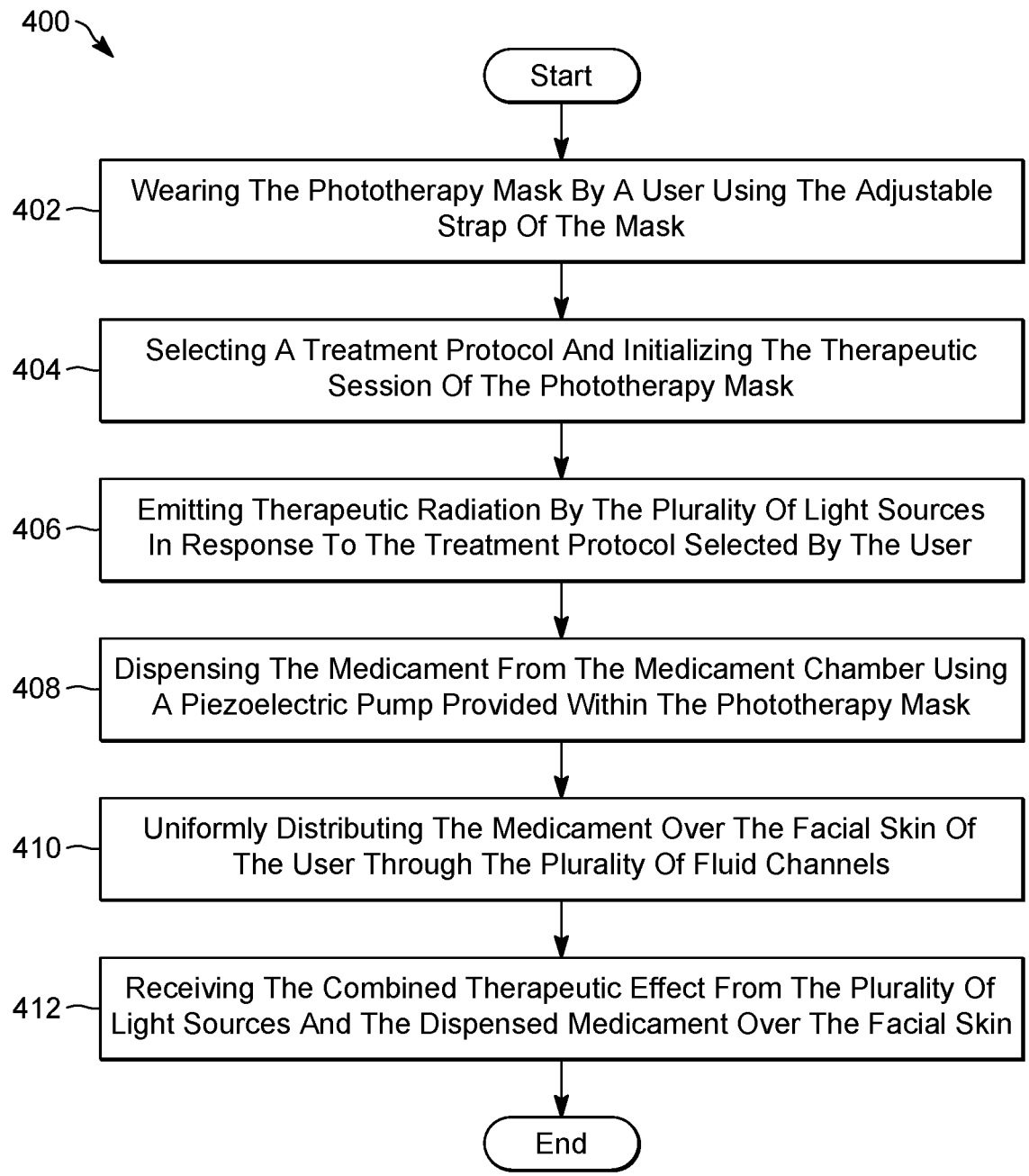
FIG. 4 illustrates a method flow diagram of the phototherapy mask in accordance with an embodiment of the present invention.

Referring now to FIG. 4 of the present invention, illustrating a method flow diagram 400 of the phototherapy mask 100 in accordance with the preferred embodiment. In the first step 402, the process of wearing the phototherapy mask 100 is disclosed, there is provided a pair of ear loops 130A and 130B though which an adjustable strap 126 (shown in FIG. 6) made of elastic material passes and detachably attached to the phototherapy mask 100. The elastic nature of the adjustable strap 126 enables the user 124 to perfectly wear the phototherapy mask 100 in accordance with their head sizes. In the second step 404, the user 124 of the phototherapy mask 100 is configured to select at least one treatment protocol and initiates the therapeutic session of the mask. Wherein, the treatment protocol preferably includes a visible mode and a non-visible mode, based on the selected mode the phototherapy mask 100 will emit therapeutic radiation. In the third step 406, the plurality of coherent light sources 108 mounted on the PCB layer 110 emits radiation towards the facial skin of the user 124 in response to the treatment protocol selected by the user 124. In the next step 408, piezoelectric pump 114 which is operably coupled to the medicament chamber 112 pumps out the predetermined amount of medicament that is stored in the medicament chamber 112. The medicament can be a photo-activating agent or can be skin-nourishing oil that nourishes or regains the elasticity of the facial skin of a user 124. In certain embodiments, the medicament may exhibit some chemical properties which enhance the efficacy of the phototherapy mask 100 when combined with light energy emitted by the plurality of light sources 108. In the fifth step 410, the medicament dispensed from the medicament chamber 112 is uniformly distributed over the facial region of the user 124 through the plurality of pores 118 present in the inner surface layer 106, and in final step 412, a combined therapeutic effect is achieved by the user 124 at the end of the session.

Figure 5:
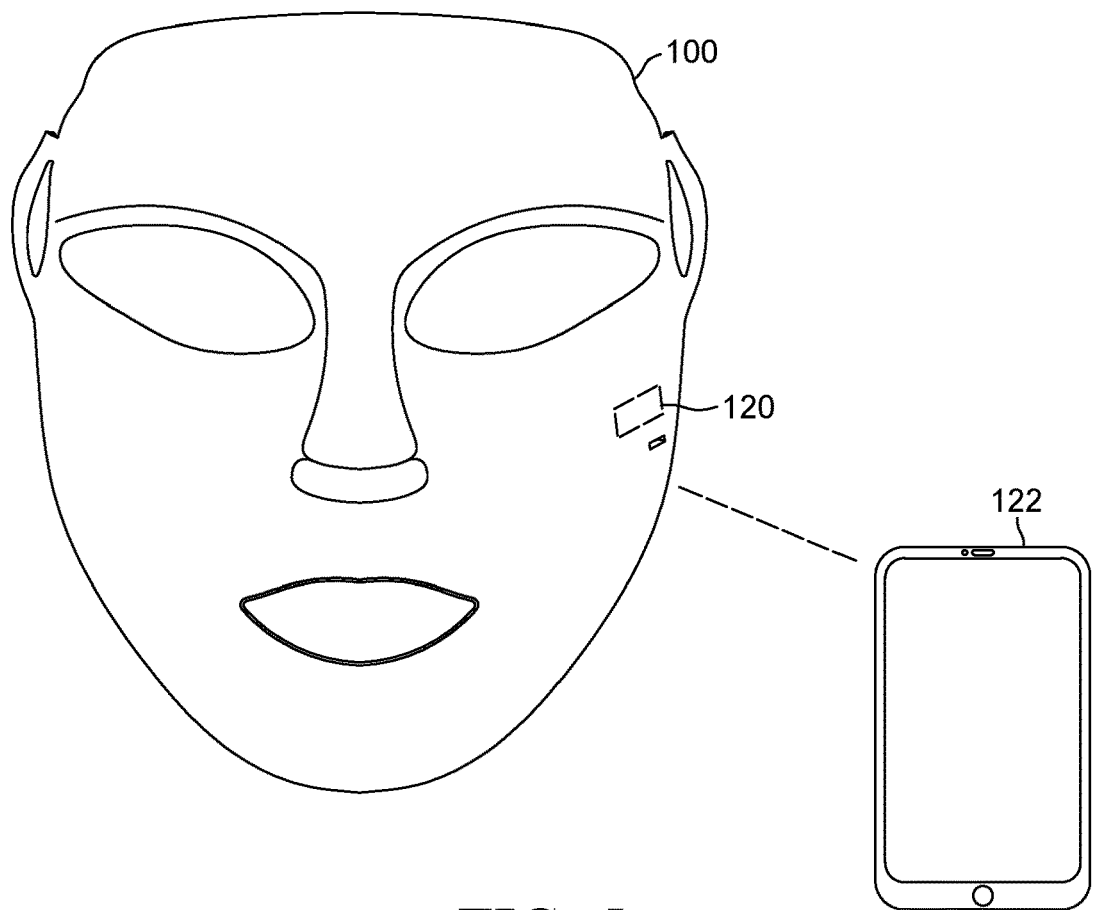
FIG. 5 illustrates a wireless communication of the phototherapy mask with an external communication device in accordance with one embodiment of the present invention.

Referring now to FIG. 5 of the present invention illustrating the connection of the phototherapy mask 100 with an external communication device 122, in accordance with an embodiment of the present invention. The external communication device 122 may be a smartphone, a desktop computer, a tablet, a Personal Digital Assistant (PDA), a smartwatch, or the like. Further, the external communication device 122 is connected with the phototherapy mask 100 through a communication network. The external communication device 122 is functionally coupled to the phototherapy mask 100 via wired or wireless connection. The external digital communication device 122 is adapted to enable the user 124 to control the functioning of the phototherapy mask 100 via the controlling unit 120. In that regard, the user input, for the control of the emission characteristics and the flow of medicament, may also be received from the external communication device 122.

Figure 6:
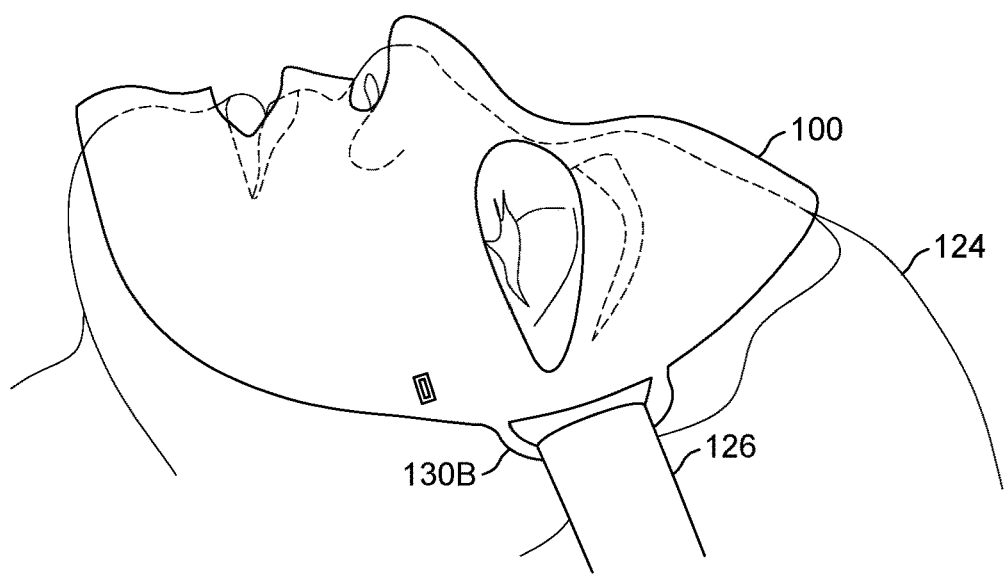
FIG. 6 illustrates a user wearing a phototherapy mask, in accordance with an embodiment of the present invention.

Referring now to FIG. 6 illustrates a user 124 is wearing the phototherapy mask 100, in accordance with an embodiment of the present invention. There is shown a pair of ear loops 130A and 130B positioned at the side portions of the phototherapy mask 100 through which an adjustable strap 126 passes. The adjustable strap 126 is preferably made of an elastic material which enables the user 124 to wear the phototherapy mask 100 comfortably. It is envisaged that extreme ends of the adjustable strap 126 are detachably attached to the phototherapy mask 100, more specifically the ends of the adjustable strap 126 are knotted with the pair of ear loops 130A and 130B through a connecting mechanism. However, the connection between the phototherapy mask 100 and the adjustable strap 126 is not limited to a particular connection mechanism, but it may include other connecting mechanisms too e.g., magnetic mechanism, snap and fit mechanism, threaded mechanism.

The present invention has been described with reference to exemplary embodiments. However, it will be readily apparent to those skilled in the art that it is possible to embody the invention in specific forms other than those of the exemplary embodiments described above. This may be done without departing from the spirit of the invention. The described embodiments are merely illustrative and should not be considered restrictive in any way. The scope of the invention is given by the appended claims and their equivalents, rather than the preceding description, and all variations and equivalents which fall within the range of the claims are intended to be embraced therein. Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A phototherapy device for producing a therapeutic response to an exposed area of human facial skin of a user, said device comprising:
 a face mask having an inner layer and an outer layer, wherein the inner layer is configured to be aligned with the facial skin of the user and includes a plurality of pores for dispensing a medicament;
 a flexible printed circuit board (PCB) provided between the inner layer and the outer layer of the device, wherein the circuit board includes a plurality of light sources that is configured to emit therapeutic radiation towards the facial skin of the user;
 a medicament chamber configured to enclose the medicament for therapeutic application onto the exposed area, the medicament chamber is configured to be positioned between the inner layer and the outer layer of the mask;
 a piezoelectric pump is operably coupled to the medicament chamber and configured to dispense the medicament through the plurality of pores of the inner layer onto the exposed area of the facial skin;
 a plurality of fluid channels provided in the inner layer of the mask, wherein the plurality of fluid channels is configured to guide flow of the medicament and uniformly distributing the medicament onto the exposed area through the plurality of pores;
 a control unit for controlling the flow of the medicament and also controls at least one characteristic of the therapeutic radiation emitted by the plurality of light sources; and a power source for providing electric power to the face mask, wherein the medicament chamber and the piezoelectric pump are located in a top region of the face mask and the plurality of fluid channels extend downwards from the medicament chamber, wherein the plurality of fluid channel comprises a main channel from the medicament chamber bifurcating into a first channel towards left forehead, a second channel towards right forehead, a third channel towards nose area, the third channel further bifurcating into a fourth channel going towards left cheek and a fifth channel going towards right cheek, wherein the first channel, the second channel, the third channel, the fourth channel and the fifth channel further bifurcates to cover the facial skin of the user.

2. The phototherapy device as claimed in claim 1, wherein the inner layer is made of synthetic polymeric material.

3. The phototherapy device as claimed in claim 2, wherein the synthetic polymer material is selected from the group consisting of a polysiloxane material and a polyacrylonitrile material.

4. The phototherapy device as claimed in claim 1, wherein the plurality of light sources includes a Light emitting diode (LED).

5. The phototherapy device as claimed in claim 1, wherein the plurality of light sources are configured to emit the therapeutic radiation in the visible range and infrared range of the electromagnetic spectrum.

6. The phototherapy device as claimed in claim 1, wherein the characteristic of emitted radiation is selected from a group consisting of intensity, frequency, amplitude, and wavelength.

7. The phototherapy device as claimed in claim 1, also supports wireless connectivity and is configured to be controlled by an external communication device.

8. The phototherapy device as claimed in claim 7, wherein the external communication device is selected from a group consisting of a cell phone, a lap-top computer, a notebook computer, a tablet computer, and a pocket computer.

9. The phototherapy device as claimed in claim 1, wherein the face mask includes a plurality of openings for nose, eye, and mouth region of the user.

10. The phototherapy device as claimed in claim 1, wherein the power source includes a rechargeable battery.

11. The phototherapy device as claimed in claim 1, wherein the face mask includes an adjustable strap allowing the user to wear the face mask comfortably.

* * * * *